United States Patent
Choque et al.

(10) Patent No.: US 6,297,409 B1
(45) Date of Patent: Oct. 2, 2001

(54) CONTINUOUS PROCESS FOR THE PREPARATION OF A HIGH-PURITY HYDROGENATED OSE BY CATALYTIC HYDROGENATION

(75) Inventors: Jean-Christophe Choque, Lille; Guy Fleche, Hazebrouck, both of (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 09/506,519

(22) Filed: Feb. 17, 2000

(30) Foreign Application Priority Data

Feb. 17, 1999 (FR) .................................... 99 02136

(51) Int. Cl.[7] .......................... C07C 31/26; C07C 31/24; C07C 31/18
(52) U.S. Cl. ........................... 568/863; 568/861; 568/881
(58) Field of Search .................................. 568/863, 881, 568/835, 857, 861; 502/326

(56) References Cited

U.S. PATENT DOCUMENTS

| | | | |
|---|---|---|---|
| 2,868,847 | 1/1959 | Boyers | 260/835 |
| 3,055,840 | 9/1962 | Koch | 252/443 |
| 3,963,789 | 6/1976 | Kruse | 260/635 C |
| 4,380,679 | 4/1983 | Arena | 568/863 |
| 4,380,680 | 4/1983 | Arena | 568/863 |
| 4,476,331 | 10/1984 | Dubeck et al. | 568/861 |
| 4,487,980 | 12/1984 | Arena | 568/863 |
| 4,626,604 | 12/1986 | Hiles et al. | 568/881 |

FOREIGN PATENT DOCUMENTS

| | | |
|---|---|---|
| 0 319 208 A1 | 11/1988 | (EP) . |
| WO 88/05767 | 8/1988 | (WO) . |

Primary Examiner—Sreem Padmanabhan
(74) Attorney, Agent, or Firm—Merchant & Gould P.C.

(57) ABSTRACT

The invention relates to a continuous process for the preparation of a high-purity hydrogenated ose by catalytic hydrogenation of the corresponding ose in falling film reactors, wherein the hydrogenation is carried out in a series of fixed beds of ruthenium catalyst comprising:

a) a first hydrogenation zone consisting of at least one fixed bed of ruthenium catalyst, and b) a second hydrogenation zone consisting of at least one fixed bed of ruthenium catalyst containing a promoter.

18 Claims, No Drawings

CONTINUOUS PROCESS FOR THE PREPARATION OF A HIGH-PURITY HYDROGENATED OSE BY CATALYTIC HYDROGENATION

The present invention relates to a continuous process for the preparation of a high-purity hydrogenated ose by catalytic hydrogenation of the corresponding ose in falling film reactors.

More particularly, the invention relates to a continuous process for the preparation of a high-purity hydrogenated ose by catalytic hydrogenation of the corresponding ose in a series of fixed beds of ruthenium catalyst arranged in two reaction zones, a first zone consisting of at least one fixed bed of ruthenium catalyst and a second zone consisting of at least one fixed bed of ruthenium catalyst containing a promoter, the whole operating in such a way as to give the hydrogenated ose with a high purity, a high degree of conversion and a high selectivity at the outlet of said second hydrogenation zone.

"Ose" is understood as meaning a carbohydrate comprising n carbon atoms and containing n-1 alcohol groups and one carbonyl group. When the carbonyl group is an aldehyde group, the ose is an aldose; when the carbonyl group is a ketone group, the ose is a ketose.

In terms of the invention, the ose has a carbon skeleton comprising n carbon atoms, n being between 3 and 7 and preferably between 4 and 6.

The ose can also belong to either the D series or the L series.

The ose can be selected especially from the group comprising aldotetroses, such as erythrose and threose, and aldopentoses or aldohexoses, such as glucose, mannose, galactose, ribose, arabinose, xylose and lyxose. The ose is preferably selected from aldoses and in particular is D-glucose.

Processes for the catalytic hydrogenation of oses are conventionally batch processes in which a pulverulent hydrogenation catalyst consisting of Raney nickel is used in suspension in the ose solution.

However, these batch processes have the disadvantage of a very low productivity and require large and expensive reactors.

Moreover, although the Raney nickel catalyst can be filtered off and re-used, a high proportion has to be replaced with fresh catalyst.

Finally, such processes remain high energy consumers.

To mitigate these disadvantages, it was proposed to carry out continuous hydrogenation processes using a plurality of cascade reactors containing pulverulent catalysts consisting of Raney nickel in suspension.

However, the activation, circulation and selective separation of said pulveruilent catalysts generally result in further substantial catalyst consumption.

Continuous processes in fixed beds of nickel/copper catalyst on an inert support were then described, but these have to be carried out under high pressure conditions and at a low surface flow velocity.

The high temperatures also used lead to isomerization and cracking reactions and to caramelization of the oses to the extent that, in the case of the hydrogenation of D-glucose, the sorbitol produced contains in particular an appreciable amount of mannitol.

One of the first continuous hydrogenation processes using one or more reactors containing nickel catalysts in a series of fixed beds is described in patent U.S. Pat No. 2,650,941.

However, the temperature and pressure conditions are still high, these conditions being necessary for attaining a degree of conversion of glucose to sorbitol in the order of 98.8%.

Other processes have been described which make it possible to increase this degree of conversion, but the formation of acids derived from oses which is inherent in the use of nickel is the main cause of catalyst deactivation and of the drop in selectivity in terms of hydrogenated reaction products.

Thus, under these conditions, gluconic acid is produced in the process for the hydrogenation of glucose, causing leaching of the metallic nickel and especially contamination, by the nickel, of the sorbitol produced.

A number of other group VIII metals, such as palladium, ruthenium and platinum, have been tested as alternative catalysts.

Thus it has been shown that palladium, ruthenium and platinum catalysis consumes less metal than nickel catalysis for a hydrogenation reaction carried out under similar temperature and pressure conditions. Ruthenium is the most efficient catalyst.

It actually affords more effective conversions, including at temperatures below 160° C. and pressure conditions in the order of 100 bar. Furthermore, it is remarkably stable under acid conditions and makes it possible, for example, to hydrogenate the gluconic acid produced during the hydrogenation reaction of glucose.

U.S. Pat. No. 2,868,847 thus describes the use of ruthenium catalysts supported on charcoal, alumina, silica or kieselguhr for the hydrogenation of carbohydrates to polyols by a batch process.

However, although this hydrogenation of glucose to sorbitol with a ruthenium catalyst makes it possible to avoid caramelization reactions and at the same time the spurious production of gluconic acid, the productivity is still too low to be economically satisfactory.

U.S. Pat. No. 4,380,679, U.S. Pat No. 4,380,680 and U.S. Pat. No. 4,487,980 describe continuous hydrogenation processes using fixed beds of ruthenium catalyst supported on charcoal, alumina or titanium dioxide, respectively, and allow the hydrogenation to be carried out under good conditions.

However, although the degrees of conversion reach 99%, the selectivities are relatively low and do not exceed 96%.

U.S. Pat. No. 3,963,789 describes the use of series of beds of ruthenium catalyst, but this process necessitates several operating cycles with acid regeneration of the catalyst and, moreover, also leads to the production of substantial amounts of isomerization products, i.e. mainly mannitol, with the sorbitol.

U.S. Pat. No. 4,476,331 also describes a multistage continuous process, the first stage consisting of a ruthenium catalyst in fixed beds and the second stage consisting of ruthenium catalysts treated with sulfur.

However, the object of this configuration is to produce sugar alcohols in the first stage and crack them in the second. For example, said patent describes the hydrogenation of hexoses to hexitols in the first stage and the cracking of said hexitols to sugar alcohols comprising 3 or 4 carbon atoms, using higher temperature conditions, in the second stage.

Patents EP 300.018, U.S. Pat. No. 4,626,604 and EP 319.208 describe multistage continuous hydrogenation processes under adiabatic conditions, using fixed beds of a group VIII catalyst, which afford degrees of conversion of aldehydes to their corresponding hydrogenated products in the order of 100%. However, it is necessary to re-introduce hydrogen at the inlet of each falling film reactor, either by itself or with fresh amounts of aldehydes to be hydrogenated. Moreover, these aldehydes are preferably compounds comprising from 7 to 17 carbon atoms of the oxoaldehyde type.

It is therefore clearly apparent in the state of the art that continuous processes for the hydrogenation of oses do not make it possible to obtain their corresponding hydrogenated products with a high purity and a high selectivity for a high degree of conversion.

In particular, these processes obligatorily involve thorough purification of the hydrogenated ose obtained in order to eliminate all traces off co-products. In the case of the hydrogenation of D-glucose to sorbitol, these co-products will be especially mannitol, arabitol and iditol.

This requirement therefore generates additional purification costs.

The aim of the invention is therefore to rectify this situation and to propose a means whereby the various practical constraints can be better satisfied and whereby, in particular, a good compromise can be reached between purity, degree of conversion and selectivity.

After numerous researches, the Applicant found that such a means could consist of a special continuous catalytic hydrogenation process in falling film reactors.

Surprisingly and unexpectedly, the Applicant found that the choice of a special ruthenium catalyst, i.e. one containing a promoter, under special conditions, i.e. in the constitution of the second hydrogenation zone, made it possible to obtain a hydrogenated ose with a high purity, a high degree of conversion and a high selectivity which had never before been achieved simultaneously by the processes described in the prior art.

In fact, all the continuous processes for the catalytic hydrogenation of oses to their corresponding hydrogenated products rather recommend using the same grades of catalyst in all the fixed beds of catalyst employed, and optimizing the hydrogenation conditions which are to enable satisfactory values to be achieved for product purity, conversion and selectivity.

To its credit the Applicant therefore showed that excellent results could be obtained by using a special combination of beds of ruthenium catalyst in series in a conventional continuous hydrogenation process in falling film reactors.

"Falling film reactor" is understood as meaning a hydrogenation reactor in which a liquid phase, containing the compound to be hydrogenated, and a gas phase flow, for example in co-current, through a fixed bed of catalyst particles, where the hydrogenation reaction takes place. The flow rates of these two phases are regulated so as to allow the liquid to trickle over the catalyst particles and to ensure a better contact between the liquid and gaseous phases on the one hand and the solid phase of the catalyst on the other.

In precise terms the present invention relates to a continuous process for the preparation of a high-purity hydrogenated ose by catalytic hydrogenation of the corresponding ose in falling film reactors, wherein the hydrogenation is carried out in a series of fixed beds of ruthenium catalyst comprising:

a) a first hydrogenation zone consisting of at least one fixed bed of uthenium catalyst, and b) a second hydrogenation zone consisting of at least one fixed bed of uthenium catalyst containing a promoter.

In terms of the invention, "high purity" is understood as meaning a degree of purity such that the proportion of hydrogenated ose obtained is equal to at least 98.3% and preferably equal to at least 98.5%, expressed as dry weight of obtained hydrogenated ose based on the total weight of hydrogenated or non-hydrogenated ose and co-products.

Throughout the specification and the claims, all the percentages are expressed by weight unless otherwise stated or clearly not applicable.

Remarkably the process according to the invention makes it possible to obtain a hydrogenated ose in which the proportion of each of the co-products of the catalytic hydrogenation reaction does not exceed a value of more than 0.5% and preferably 0.3%.

By way of example, the catalytic hydrogenation of D-glucose to sorbitol by the process according to the invention makes it possible to limit the formation of each of the main co-products of the hydrogenation reaction, i.e. iditol, arabitol and mannitol, to a value in the order of 0.25%.

In the process according to the invention, a solution of ose to be hydrogenated is therefore passed through a first hydrogenation zone consisting of at least one fixed bed of ruthenium catalyst. It is preferable to choose a single fixed bed of ruthenium catalyst placed in a falling film reactor.

The solution of partially hydrogenated ose is then led into the second hydrogenation zone consisting of at least one fixed bed of ruthenium catalyst containing a promoter. It is preferable to choose a single fixed bed of catalyst in this second falling film reactor.

The fixed beds of catalyst are composed of a compact stack of particles containing ruthenium impregnated or co-exchanged on an inert support.

This inert support can be selected from the group consisting of active charcoal, zeolites, aluminosilicate and titanium dioxide; it preferably consists of active charcoal.

The weight ratio of ruthenium to inert support is fixed at a value of between and 5% and preferably of between 1 and 2%.

In the second hydrogenation zone the fixed bed or beds of catalyst consist of ruthenium containing a promoter.

This promoter is selected from the group consisting of titanium, molybdenum, platinum and chromium. It preferably consists of platinum.

The value of the weight ratio of promoter to inert support constituting the fixed bed of catalyst is then chosen between 0.1 and 0.3% and is preferably in the order of 0.2%.

In the process according to the invention, the first hydrogenation zone is fed with an ose solution whose solids content is generally between 20 and 50% and preferably between 30 and 50%.

In one preferred embodiment of the process according to the invention, the ose is selected from the group consisting of erythrose, threose, glucose, mannose, galactose, ribose, arabinose, xylose, lyxose and all their isomers with a ketone group. Preferably, D-glucose is chosen as the ose to be hydrogenated and the solids content of said solution is in the order of 40%.

The feed rate of the solutions of ose to be hydrogenated per catalyst bed, in the process according to the invention, is between 0.3 and 2 kg/l/h and preferably between 1 and 1.5 kg/l/h, expressed as kg of ose solution per liter of fixed bed of catalyst and per hour.

By way of example, for a D-glucose solution with a solids content of between 30 and 50% and preferably in the order of 40%, the feed rate can be set at a value in the order of 1.2 kg/l/h.

The surface flow velocity of the solution of ose to be hydrogenated inside said fixed beds of catalyst is maintained at a value of between about 0.02 and 0.2 cm/s and preferably at a value in the order of 0.1 cm/s.

The hydrogenation temperature and pressure conditions are also controlled so as to direct the hydrogenation of the ose to its corresponding hydrogenated product with a high purity, a high degree of conversion and a high selectivity.

The temperature conditions are thus controlled at values below 120° C. and preferably of between 80 and 105° C.

The hydrogen pressure conditions are also set at values of at least 50 bar and preferably of between 50 and 150 bar.

By way of example, for the hydrogenation of D-glucose to sorbitol, the hydrogenation temperature can be in the order of 98° C. at the end of the first hydrogenation zone and in the order of 99° C. at the end of the second hydrogenation zone. The pressure is maintained at 100 bar, as exemplified below.

The Applicant also showed that the hydrogen flow rate, in the process according to the invention, must be such that the amount of hydrogen introduced is at least five times and preferably at least ten times greater than the stoichiometry of the reaction.

In one preferred embodiment of the invention, the hydrogenation conditions, i.e. the feed rate, the solids content of the solution of ose to be hydrogenation, the hydrogenation temperature and pressure conditions and the hydrogen flow rate, are regulated so as to effect substantial hydrogenation of the ose to its hydrogenated product at the end of the first hydrogenation zone.

In terms of the invention, "substantial hydrogenation" is understood as meaning hydrogenation which makes it possible to achieve a degree of conversion of between about 70 and 95% and preferably of between 80 and 95%.

This solution of partially hydrogenated ose is then introduced into the second hydrogenation zone, and by keeping the operating conditions identical to those used in the first hydrogenation zone, with the exception of the constitution of the fixed bed of ruthenium catalyst, a high-purity hydrogenated ose can be obtained with a high degree of conversion, for example of at least 99.85%, and also with a high selectivity, for example of at least 98% and preferably of at least 99%.

Other characteristics and advantages of the invention will become apparent from the non-limiting Examples described below.

EXAMPLE 1

The hydrogenation reaction is carried out in two falling film reactors, connected in series, with 1 intermediate heat exchanger.

The two reactors each contain a single fixed bed of catalyst, namely ruthenium and ruthenium/platinum respectively, through which hydrogen and D-glucose solution are circulated in co-current from the top to the bottom of said reactors. No additional hydrogen needs to be introduced at the inlet of the second hydrogenation zone.

Each fixed bed of ruthenium catalyst consists of a compact stack of cylindrical catalyst granules.

Each catalyst granule is composed of NORIT RX08 active charcoal in the form of a cylinder 0.8 mm in diameter and 1 to 5 mm in length, on which the noble metals ruthenium, in the first falling film reactor, and ruthenium/platinum, in the second falling film reactor, are in respective proportions of 2.11% ruthenium and 1.15% ruthenium/0.2% platinum.

Each reactor contains 250 l of catalyst placed in a fixed bed 30 cm in diameter and 3.5 m in height.

The first hydrogenation zone is fed simultaneously with a commercial D-glucose solution, with a solids content of 40%, at a rate of 1.2 kg/l/h and with hydrogen at a rate of 15 kg/h.

The operating pressure is 100 bar and the preheating temperatures are adapted to give temperatures of 98° C. and 99° C. at the outlets of the first and second reactors, respectively.

The degree of conversion of the D-glucose to sorbitol is found to have a value of 90.5% after analysis of the hydrogenation products by gas chromatography.

The hydrogenated syrup at the outlet of the second reactor has the composition given in Table I below.

TABLE I

| Sugar alcohols ultimately produced | % dry/dry |
|---|---|
| Sorbitol | 98.9 |
| Mannitol | 0.25 |
| Iditol | 0.25 |
| Arabitol | 0.25 |

A sorbitol of high purity, i.e. in the order of 98.9%, is obtained with a particularly high selectivity and degree of conversion.

The selectivity of the reaction is in fact 99.2%. It is especially remarkable that none of the main co-products is present with the sorbitol in a proportion greater than 0.3%. Moreover, there is no significant production of maltitol, isomaltitol or gluconic acid.

The proportion of free reducing sugars, assayed by the SOMOGY method, is 500 ppm, which corresponds to a degree of conversion of 99.95%.

EXAMPLE 2

Table II below summarizes the results obtained from the continuous hydrogenation process of Example 1 according to the invention, compared with the results obtained under the same hydrogenation operating conditions except that no promoter is added to the ruthenium which makes up the fixed bed of catalyst constituting the second falling film reactor.

TABLE II

| | | |
|---|---|---|
| First zone | 2.11% Ru | 2.11% Ru |
| Second zone | 2.11% Ru | 1.15% Ru/0.2% Pt |
| Sorbitol (%) | 98.2 | 98.9 |
| Mannitol (%) | 0.4 | 0.25 |
| Arabitol (%) | 0.3 | 0.25 |
| Iditol (%) | 0.5 | 0.25 |
| Degree of conversion (%) | 99.8 | 99.95 |
| Selectivity (%) | 98.5 | 99.2 |

In the absence of promoter, the three main co-products of the hydrogenation reaction of D-glucose to sorbitol in fixed beds of ruthenium-only catalyst are each in a proportion equal to at least 0.3%.

The results clearly show the technological advantage, in terms of purity and selectivity at high degrees of conversion, which is afforded by using the continuous catalytic hydrogenation process according to the invention.

What is claimed is:

1. A continuous process for the preparation of a high-purity hydrogenated ose by hydrogenation of the corresponding ose in falling film reactors, comprising performing the hydrogenation in a series of fixed beds of ruthenium catalyst comprising:

a) a first hydrogenation zone consisting of at least one fixed bed of ruthenium catalyst, and b) a second hydrogenation zone consisting of at least one fixed bed of ruthenium catalyst containing a promoter.

2. The process of claim 1, wherein the promoter used with the ruthenium catalyst in the second hydrogenation zone is selected from the group consisting of titanium, molybdenum, platinum and chromium.

3. The process of claim 1, wherein the promoter is platinum.

4. The process of claim 1, wherein the ose is selected from the group consisting of erythrose, threose, glucose, mannose, galactose, ribose, arabinose, xylose, lyxose, and any isomer of anyone of said ose with a ketone group.

5. The process of claim 1, wherein said ose is D-glucose.

6. The process of claim 1, wherein the first hydrogenation zone is fed with an ose solution whose solids content is ranging between 20 and 50% by weight.

7. The process of claim 1, wherein the first hydrogenation zone is fed with an ose solution whose solids content is ranging between 30 and 50% by weight.

8. The process of claim 1, wherein, in each of the hydrogenation zones, the feed rate of the solution of ose to be hydrogenated is ranging between 0.3 and 2kg/l/h.

9. The process of claim 1, wherein, in each of the hydrogenation zones, the feed rate of the solution of ose to be hydrogenated is ranging between 1 and 1.5 kg/l/h.

10. The process of claim 1, wherein the surface flow velocity of the liquid passing through the beds of ruthenium catalyst arranged in series in the two hydrogenation zones is ranging between 0.02 and 0.2 cm/s.

11. The process of claim 1, wherein the surface flow velocity of the liquid passing through the beds of ruthenium catalyst arranged in series in the two hydrogenation zones is of about 0.1 cm/s.

12. The process of claim 1, wherein the temperature in the two hydrogenation zones is below 120° C., and wherein the hydrogen pressure in the two hydrogenation zones is at least 50 bar.

13. The process of claim 1, wherein the temperature in the two hydrogenation zones is ranging between 80 and 105° C. and wherein the hydrogen pressure in the two hydrogenation zones is ranging between 80 and 150 bar.

14. The process of claim 1, wherein the hydrogen flow rate is selected to provide an amount of hydrogen introduced of at least five times greater than the stoichiometry of the reaction.

15. The process of claim 1, wherein the hydrogen flow rate is selected to provide an amount of hydrogen introduced of at least ten times greater than the stoichiometry of the reaction.

16. The process of claim 1, wherein the hydrogenated ose is sorbitol.

17. The process of claim 1, wherein the hydrogenated ose is sorbitol with a purity of at least 98.3% expressed as dry weight of obtained hydrogenated ose based on the total weight of hydrogenated, ose non-hydrogenated ose and co-products.

18. The process of claim, wherein the hydrogenated ose is sorbitol with a purity of at least 98.5% by expressed as dry weight of obtained hydrogenated ose based on the total weight of hydrogenated, ose non-hydrogenated ose and co-products.

* * * * *